US00PP13194P2

(12) United States Plant Patent
Heims

(10) Patent No.: US PP13,194 P2
(45) Date of Patent: Nov. 5, 2002

(54) CAMPANULA PLANT NAMED 'BOWL OF CHERRIES'

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/967,087

(22) Filed: Sep. 27, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Campanula plant characterized by a dwarf habit and deep red purple flowers.

1 Drawing Sheet

BOTANICAL CLASSIFICATION

*Campanula punctata.*

VARIETY DENOMINATION

'Bowl of Cherries'.

The present invention relates to a new and distinct hybrid of *Campanula punctata*, of the family Campanulaceae, which originated as a cross between *Campanula punctata nana alba* (seed parent) and *Campanula punctata* 'Cherry Bells' (pollen parent).

The new variety has been reproduced only by asexual propagation (division and tissue culture). Each of the progeny exhibits identical characteristics to the original plant.

This plant is characterized by the following:

1. Dwarf habit.

2. Numerous, deep red purple flowers held over the foliage.

3. Strong, short flowering stems that don't fall over.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The FIGURE shows Campanula 'Bowl of Cherries' growing in the field in Canby, Oreg.

DETAILED PLANT DESCRIPTION

The following is a detailed description of the new Campanula hybrid based on observations of a two year old specimen grown in the field in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—31 cm. wide and 12 cm. tall.
- *Form.*—Basal clump.

Leaf:
- *Type.*—Simple.
- *Shape.*—Ovate-cordate.
- *Arrangement.*—Rosette.
- *Blade length.*—3 to 5.7 cm.
- *Blade width.*—2.1 to 3.5 cm. at the widest part.
- *Margins.*—Doubly serrate, undulate.
- *Apex.*—Acuminate.
- *Base.*—Cordate.
- *Texture.*—Hispid on the top and bottom.
- *Venation.*—Pinnate.
- *Petiole length.*—7.5 to 11.5 cm., clasping at the base.
- *Petiole texture.*—Hispid.
- *Petiole color.*—Greyed Purple 183A except some bases are Yellow Green 144B and lighter.
- *Color.*—Topside — Green 137A. Sometimes veins are Greyed Purple 183A. Bottom — Yellow Green146B.

Inflorescence:
- *Type.*—Terminal panicle.
- *Peduncle.*—Height: 12 to 35 cm. Diameter: 0.2 cm. at widest. Texture: Hispid. Color: Maroon, Greyed Purple 187A.
- *Cauline leaves.*—Size: 4 to 6 cm long and 1.5 cm wide with petioles winged or no petiole on uppermost. Shape: Ovate. Color: With main vein usually Greyed Purple 183B on leaf Green 137A with Brown 200B edges.
- *Pedicel.*—Length: 0.5 to 5.5 cm. Texture: Hispid. Color: Yellow Green 146B or Greyed Purple 184A or mixed.
- *Flower number.*—16 per panicle.

Flower bud:
- *Size.*—4.5 cm. deep and 1.8 cm. wide.
- *Shape.*—Ovoid, pentagonal in cross section.
- *Color.*—Closest to Red Purple 71A but deeper in color.
- *Texture.*—Glabrous.

Flower:
- *Type.*—Actinomorphic.
- *Shape.*—Campanulate.
- *Size.*—5.5 cm deep and 2.5 cm. wide.
- *Corolla.*—Inflated tube with 5 acute lobes that reflex back at tips. Lobes are 0.8 cm deep and 1.2 cm wide at the base.
- *Texture.*—Glabrous except villous on lobe margins.
- *Color.*—Deep red purple. Red Purple 71A on outside and inside so heavily spotted with Red Purple 71A that it appears light purple with the heaviest spotting at the veins.

*Calyx.*—5 deeply cut acuminate lobes, ovate lanceolate, parted ⅔ to base, with basal lobes reflexed all the way back to the pedicel.

*Calyx size.*—2.5 cm deep and 2.3 cm wide.

*Calyx color.*—Yellow Green 144A on inside and outside base, mottled maroon appearing Greyed Purple 183A in bright sun.

*Pistil.*—3.3 cm. long, White 155A and lavender, Purple 76C, stigma 3-parted.

*Stamen number.*—5.

*Filament length.*—0.4 cm.

*Anther size before dehiscing.*—0.8 cm.

*Pollen color.*—Light Orange 27D.

*Bloom period.*—May through July in Canby, Oreg. It will rebloom when cut back if climates are mild.

*Fragrance.*—None.

Fruit:

*Type.*—3-celled capsule.

*Color.*—Tan, Grey Brown 199D.

Seed:

*Color.*—Grey Brown 199A.

*Size.*—Approximately 1 mm. long.

*Shape.*—Oval.

*Fertility.*—Fertile.

Disease: None observed on plant grown under commercial conditions in Canby, Oreg.

COMPARISONS TO SIMILAR CAMPANULA

Compared to *Campanula punctata* 'Cherry Bells', an unpatented plant, this new cultivated variety has a dwarfed habit, better suited to potted plant culture.

Compared to *Campanula punctata* 'Pink Chimes' (Plant patent application Ser. No. 09/967,085, filed Sep. 27, 2001), this new cultivated variety has much darker flowers of an overall dark red purple rather than a pink appearance.

I claim:

1. A new and distinct hybrid of Campanula plant substantially as shown and described, characterized by a dwarf habit and deep red purple flowers.

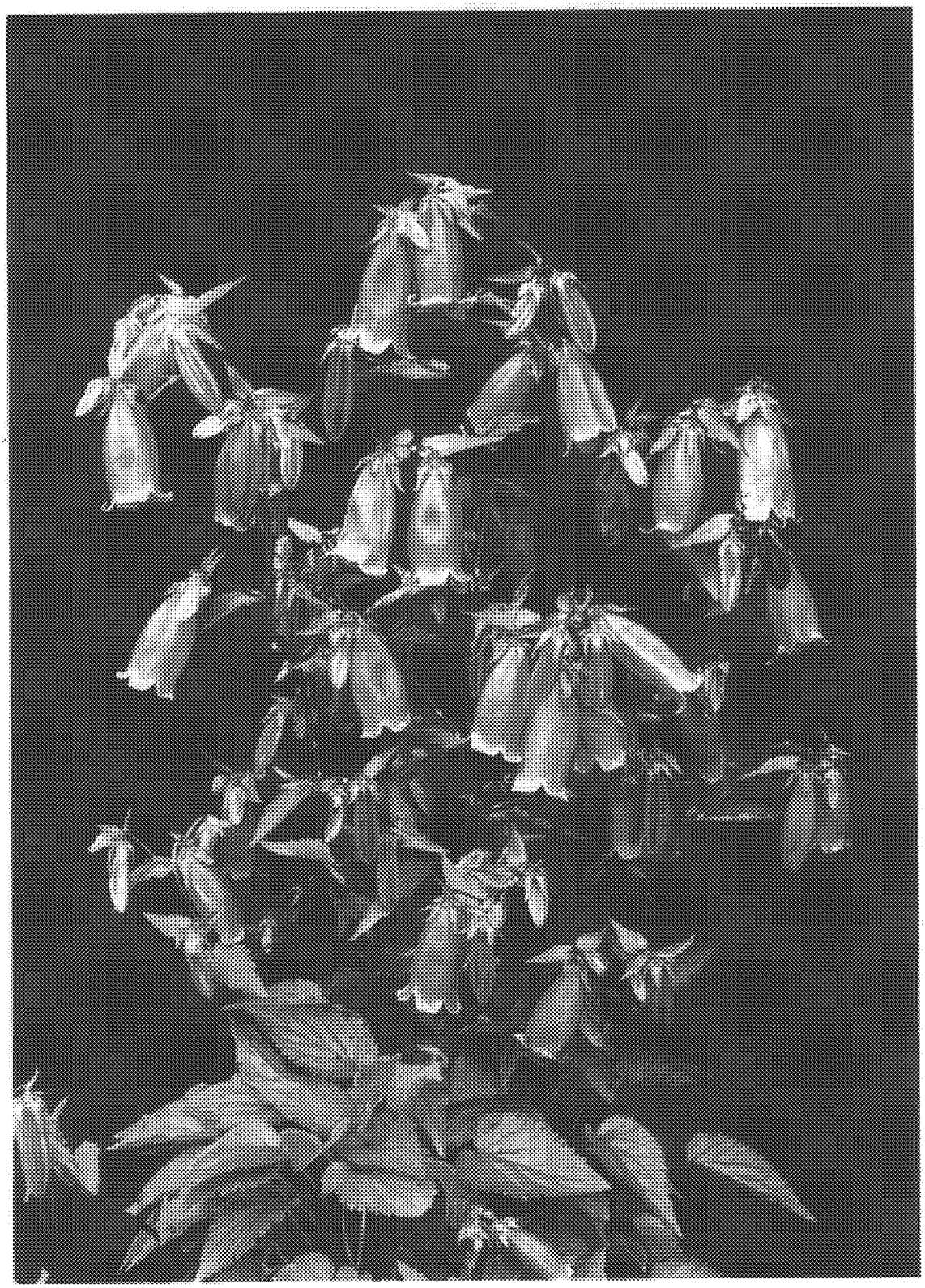

* * * * *